US012788793B2

(12) United States Patent
Choi

(10) Patent No.: US 12,788,793 B2
(45) Date of Patent: Nov. 10, 2026

(54) BONCHONGMYUNGTANG COMPOSITION FOR IMPROVING MEMORY AND LEARNING ABILITY

(71) Applicant: Jeongwoo Choi, Seoul (KR)

(72) Inventor: Young-jin Choi, Seoul (KR)

(73) Assignees: Young-Jin Choi, Seoul (KR); Jeongwoo Choi, Seoul (KR)

( * ) Notice: Subject to any disclaimer, the term of this patent is extended or adjusted under 35 U.S.C. 154(b) by 110 days.

(21) Appl. No.: 19/083,511

(22) Filed: Mar. 19, 2025

(65) Prior Publication Data

US 2025/0302905 A1 Oct. 2, 2025

(30) Foreign Application Priority Data

Mar. 27, 2024 (KR) ........................ 10-2024-0041971

(51) Int. Cl.

*A61K 36/69* (2006.01)
*A61K 9/00* (2006.01)
*A61K 36/18* (2006.01)
*A61K 36/346* (2006.01)
*A61K 36/882* (2006.01)
*A61K 36/8969* (2006.01)
*A61K 47/02* (2006.01)
*A61P 25/28* (2006.01)

(52) U.S. Cl.

CPC ............ *A61K 36/69* (2013.01); *A61K 9/0053* (2013.01); *A61K 36/18* (2013.01); *A61K 36/346* (2013.01); *A61K 36/882* (2013.01); *A61K 36/8969* (2013.01); *A61K 47/02* (2013.01); *A61P 25/28* (2018.01); *A61K 2236/331* (2013.01); *A61K 2236/37* (2013.01)

(58) Field of Classification Search

None

See application file for complete search history.

(56) References Cited

FOREIGN PATENT DOCUMENTS

| | | |
|---|---|---|
| KR | 10-0524385 B1 | 11/2005 |
| KR | 10-0530211 B1 | 11/2005 |
| KR | 10-2008-0107922 A | 12/2008 |

OTHER PUBLICATIONS

Ameer (Journal of Pharmacopuncture (2015), No. 18, No. 1, pp. 7-18).*
Ji (Foods (2020), vol. 9, No. 142, 19 pages).*
Liu (CN 1279090 A)—2001.*
Decision to Grant issued in corresponding KR Patent Application No. 10-2024-0041971, dated Nov. 11, 2024, with a copy of the registered claims.
Korean Office Action issued in corresponding KR Patent Application No. 10-2024-0041971, dated May 19, 2024, with English translation.
Park, E-K et al., "Effects of Chongmyung-tang, Polygalae Radix and Acori Graminei Rhizoma on AB Toxicity and Memory Dysfunction in Mice" Korean J. Orient. Int. Med. (2008) pp. 608-620, vol. 29, No. 3, with English abstract.
Kim, E-S et al., "Protective Effects of Polygonatum odoratum Extracts on Amyloid B-protein-induced Death in Neuronal Cells" Cancer Prevention Research (2008) pp. 197-204, vol. 13, No. 3, with English abstract.
Kim, T-E et al., "The Effect of Femented Platycodon grandiflorum on the Memory Impairment of Mice" Kor. J. Herbology (2013) pp. 25-31, vol. 28, No. 2, with English abstract.
Written Opinion submitted in response to the Korean Office Action issued in corresponding KR Patent Application No. 10-2024-0041971, submitted on Jul. 9, 2024, English translation.

* cited by examiner

*Primary Examiner* — Susan Hoffman

(74) *Attorney, Agent, or Firm* — Carter, DeLuca & Farrell LLP; George Likourezos

(57) ABSTRACT

A pharmaceutical composition for improving memory and learning ability according to one embodiment of the present invention includes, as an active ingredient, an extract of a mixed herbal medicine including Polygalae Radix, Acori Graminci Rhizoma, Platycodonis Radix, Polygonati Rhizoma, and Loranthi Ramulus Et Folium.

3 Claims, 12 Drawing Sheets

BONCHONGMYUNGTANG COMPOSITION FOR IMPROVING MEMORY AND LEARNING ABILITY

CROSS-REFERENCE TO RELATED APPLICATION

This application claims priority to Korean Patent Application No. 10-2024-0041971 filed on Mar. 27, 2024 and all the benefits accruing therefrom under 35 U.S.C. § 119, the contents of which are incorporated by reference in their entirety.

BACKGROUND

The present disclosure relates to a pharmaceutical composition for improving memory and learning ability.

As the social environment becomes more diverse, people are exposed to more stimuli, and thus require quick brain activity in order to accommodate many stimuli. In addition, the aging population resulting from improved living standards and scientific advancements has led to an increase in chronic degenerative diseases, such as memory decline, forgetfulness, and increased anxiety, due to degraded central nervous system function. In addition, for adolescents, prolonged learning activities may lead to mental and physical fatigue, negatively affecting healthy brain development, and the heavy academic burden on growing students has become a social issue.

Therefore, as society becomes more complex and competition for entrance exams intensifies, there is a need for the development of a method capable of clearing a fatigued brain, thereby enhancing memory, and promoting recovery from fatigue.

In response to the above-described demand from the society, products for improving learning ability, cognitive function, and memory have been developed, and particularly, products typically developed often use compounds synthesized to stimulate brain nerves so as to improve learning ability and memory, but due to various side effects, recent efforts have focused on developing products using natural materials.

When examining related compositions using natural materials, Korean Registration Patent No. 10-0524385 discloses a composition for enhancing memory and improving learning ability in adolescents, the composition containing a complex herbal medicine extract of Longanae Arillus, Zizyphi Semen, Polygalae Radix (*Polygala tenuifolia* Willdenow), and Hoelen cum Pini Radix, and Korean Registration Patent No. 10-0530211 discloses a health functional food composition for improving learning ability, the composition containing natural materials such as Cassiae Semen, Rehmanniae Radix Preparata, Poria, Achyranthis Radix, *Dioscoreae* Rhizoma, Cistanche *deserticola* Y. C. Ma, *Morindae* Radix, *Cinnamomi* Cortex, Epimedii Herba, Psoralea corylifolia L., Astragali Radix, Angelicae Gigantis Radix, Eucommiae Cortex, *Broussonetiae* Fructus, Polygalae Radix (*Polygala tenuifolia* Willdenow), Acori Graminei Rhizoma (Acorus gramineus Solander), Corni Fructus, *Zingiber officinale*, and Zizyphi Fructus.

These prior documents are forms in which other natural materials are supplemented to a typically known Chongmyungtang composition of Polygalae Radix, Acori Graminei Rhizoma, and Hoelen cum Pini Radix, and there is a limitation in improving memory, improving learning ability, and improving cognitive function due to insignificant effects of improving memory, improving learning ability, and improving cognitive function.

PRIOR ART DOCUMENT

Patent Literature

Korean Patent Registration No. 10-0524385
Korean Patent Registration No. 10-0530211

SUMMARY

The present disclosure provides a pharmaceutical composition with an excellent memory improvement effect.

The present disclosure also provides a pharmaceutical composition with an excellent learning ability improvement effect.

The present disclosure also provides a pharmaceutical composition with an excellent cognitive function improvement effect.

The present disclosure also provides a pharmaceutical composition with minimum side effects.

In addition to the above-mentioned objectives, embodiments according to the present invention may be used to achieve other objectives not specifically mentioned.

In accordance with an exemplary embodiment of the present invention, a pharmaceutical composition for improving memory and learning ability includes, an extract of a mixed herbal medicine including Polygalae Radix, Acori Graminei Rhizoma, Platycodonis Radix, Polygonati Rhizoma, and Loranthi Ramulus Et Folium as an active ingredient, and a carrier, wherein the carrier is at least one of saline, sterilized water, Ringer's solution, buffered saline, dextrose solution, maltodextrin solution, glycerol, ethanol, or a mixture of one or more of these ingredients.

In the mixed herbal medicine, the weight ratio of the Polygalae Radix, the Acori Graminei Rhizoma, the Platycodonis Radix, the Polygonati Rhizoma, and the Loranthi Ramulus Et Folium may be 1:1:1:1:0.5 to 1.

In accordance with another exemplary embodiment of the present invention, a medication for improving memory and learning ability includes the above-described pharmaceutical composition.

In accordance with another exemplary embodiment of the present invention, a health functional food composition for improving memory and learning ability includes, an extract of a mixed herbal medicine including Polygalae Radix, Acori Graminei Rhizoma, Platycodonis Radix, Polygonati Rhizoma, and Loranthi Ramulus Et Folium as an active ingredient, and a carrier, wherein the carrier is at least one of saline, sterilized water, Ringer's solution, buffered saline, dextrose solution, maltodextrin solution, glycerol, ethanol, or a mixture of one or more of these ingredients.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
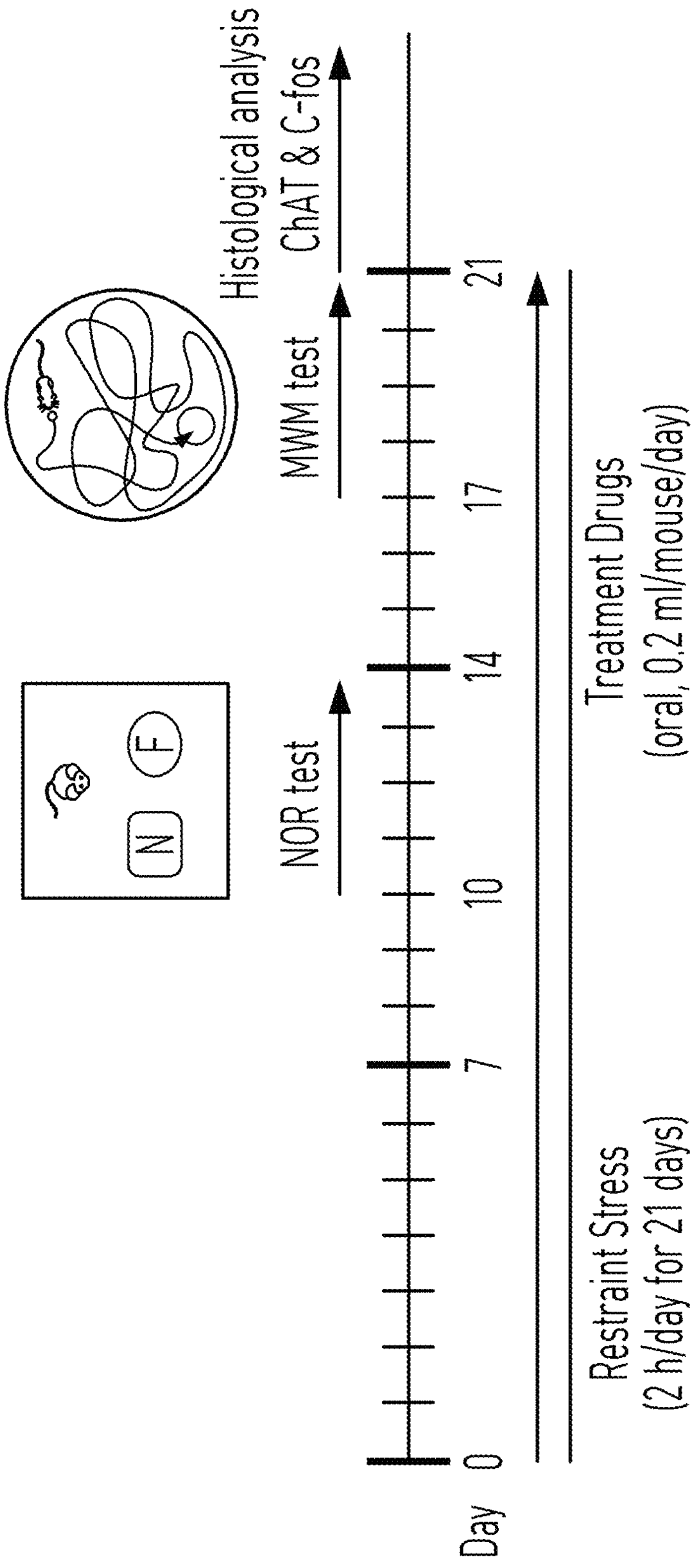
FIG. 1 is a diagram showing an experimental sequence and procedure for experimental target mice administered with compositions according to examples and comparative examples.

With reference to the accompanying drawings, embodiments of the present invention will be described in detail so that those skilled in the art can easily carry out the present invention. The present invention may be embodied in many different forms, and is not limited to the embodiments set forth herein. In order to clearly describe the present invention, parts irrelevant to the description are omitted in the drawings, and like reference numerals are used for the same or like elements throughout the specification. In addition, in the case of well-known technologies, a detailed description thereof will be omitted.

Throughout the specification, when a portion is said to "include" any element, it means that the portion may further include other elements rather than excluding the other elements unless otherwise stated.

Throughout the specification, a "composition" refers to a material in which two or more ingredients are uniformly mixed, and is a concept including not only a finished product but also an intermediate material for manufacturing the finished product.

The present invention relates to a novel composition having an excellent effect of improving memory, improving learning ability, and improving cognitive function.

In addition, a pharmaceutical composition according to the embodiments is based on natural medicinal ingredients, and thus, may be harmless to the human body and have excellent safety, and includes a plurality of materials not exhibiting toxicity, and thus, may minimize side effects.

The pharmaceutical composition for improving memory and improving learning ability according to the embodiments includes, as an active ingredient, an extract of a mixed herbal medicine including Polygalae Radix (*Polygala tenuifolia* Willdenow), Acori Graminei Rhizoma (Acorus gramineus Solander), Platycodonis Radix (Platycodon *grandiflorum* A. De Candolle), and Polygonati Rhizoma (*Polygonatum kingianum* Coll. et Hemsley).

The pharmaceutical composition may improve memory, may improve cognitive function, and may also improve learning ability.

Meanwhile, Choline Acetyltransferase (ChAT) of a hippocampus of a brain is an enzyme for synthesizing acetylcholine, which is a neurotransmitter in the hippocampus, and if acetylcholine is reduced, the activity of nerve cells is reduced, resulting in reducing memory, but the pharmaceutical composition according to the embodiment may improve memory by increasing the expression of the ChAT.

In addition, when the brain is stressed, a Hypothalamic-Pituitary-Adrenal Axis (HPA axis) is activated, and a paraventricular nucleus (PVN) of a hypothalamus is activated, wherein the PVN synthesizes a corticotropin-releasing hormone (CRH) and secretes the same into a pituitary gland, and a stimulated anterior pituitary gland secretes an adrenocorticotropic hormone (ACTH), and an adrenal cortex responds to the stimulation of the ACTH to produce cortisol, which is known as a stress hormone. The produced cortisol spreads throughout the body via the bloodstream, and induces a stress response of the body. As described above, the activation of the PVN in the stress response plays a very important role in regulating stress. At this time, C-fos protein, which is an immediate early gene, is expressed in the PVN, and the pharmaceutical composition according to the embodiment may reduce the expression of the C-fos protein increased in the PVN, and as a result, memory, learning ability, and cognitive function may be improved.

Typically, in relation to the effect of enhancing memory, Polygalae Radix and Acori Graminei Rhizoma have been known as components of Chongmyungtang, but in the case of Platycodonis Radix and Polygonati Rhizoma, there has been no disclosure or teaching regarding effects of enhancing memory and improving learning ability.

A mixed herbal medicine composition including Polygalae Radix, Acori Graminei Rhizoma, Platycodonis Radix, and Polygonati Rhizoma is a novel combination not disclosed in the prior art, and a pharmaceutical composition containing an extract of a herbal medicine having such a composition also corresponds to a novel composition not disclosed in the prior art.

In addition, when the mixed herbal medicine includes all of Polygalae Radix, Acori Graminei Rhizoma, Platycodonis Radix, and Polygonati Rhizoma, the pharmaceutical composition may have better effects of improving memory, improving learning ability, and improving cognitive function due to the synergistic effect.

Based on the total weight of the mixed herbal medicine, the weight ratio of Polygalae Radix, Acori Graminei Rhizoma, Platycodonis Radix, and Polygonati Rhizoma may be about 1:1:1:1, and in such a weight ratio, the effects of improving memory, improving learning ability, and improving cognitive function may be further increased.

The mixed herbal medicine of the pharmaceutical composition may further include Loranthi Ramulus Et Folium (*Loranthus chinensis* Danser). The Loranthi Ramulus Et Folium (*Loranthus chinensis* Danser) corresponds to a material having no known effects of improving memory, improving learning ability, and improving cognitive function.

In the case of the pharmaceutical composition according to the embodiment, an extract of the Loranthi Ramulus Et Folium generates an additional synergistic effect, so that the effects of improving memory, improving learning ability, and improving cognitive function of the pharmaceutical composition may be further improved.

In addition, the mixed herbal medicine composition including Polygalae Radix (*Polygala tenuifolia* Willdenow), Acori Graminei Rhizoma (*Acorus gramineus* Solander), Platycodonis Radix (Platycodon *grandiflorum* A. De Candolle), Polygonati Rhizoma (*Polygonatum kingianum* Coll. et Hemsley), and Loranthi Ramulus Et Folium (*Loranthus chinensis* Danser) corresponds to a combination different from the prior art, and a pharmaceutical composition including an extract of a herbal medicine having such a composition also corresponds to a novel composition.

When the mixed herbal medicine includes all of Polygalae Radix, Acori Graminei Rhizoma, Platycodonis Radix, Polygonati Rhizoma, and Loranthi Ramulus Et Folium, the pharmaceutical composition may have better effects of improving memory, improving learning ability, and improving cognitive function due to the synergistic effect. In addition, when the mixed herbal medicine includes all of Polygalae Radix, Acori Graminei Rhizoma, Platycodonis Radix, Polygonati Rhizoma, and Loranthi Ramulus Et Folium, compared to a case of a mixed herbal medicine including Polygalae Radix, Acori Graminei Rhizoma, Platycodonis Radix, and Polygonati Rhizoma, better effects of improving memory, improving learning ability, and improving cognitive function may be exhibited.

Based on the total weight of the mixed herbal medicine, the weight ratio of Polygalae Radix, Acori Graminei Rhizoma, Platycodonis Radix, Polygonati Rhizoma, and Loranthi Ramulus Et Folium may be about 1:1:1:1:0.5 to 1, and in such a weight ratio, the effects of improving memory, improving learning ability, and improving cognitive function may be further improved.

The pharmaceutical composition according to the embodiments may exhibit an effect of preventing, alleviating, or treating forgetfulness or dementia, and may be used for preventing, alleviating, or treating forgetfulness or dementia.

In addition, since the pharmaceutical composition contains, as an active ingredient, a mixed herbal medicine extract having almost no toxicity or side effects, the pharmaceutical composition may be safe to be used even for long-term administration for preventive purposes.

Meanwhile, the pharmaceutical composition may include another pharmaceutically active ingredient other than the above-described ingredients, or may be mixed with a pharmaceutical composition including another active ingredient and used.

In order to prepare the pharmaceutical composition including the mixed herbal medicine extract, those skilled in the art may use any suitable method known in the art.

For example, a step of preparing a mixed herbal medicine and a step of performing hot water extraction are performed.

The hot water extraction may be performed, for example, at 80° C. to 140° C. for 2 hours to 3 hours, and in the above-described ranges, extraction may be effectively performed without destroying or deteriorating constituents of an extract. In this case, the weight of water may be about 5 times to 10 times the weight of the mixed herbal medicine.

Next, a step of filtering the extract obtained by the hot water extraction using a membrane filter is performed. In this case, the membrane filter may have an average pore size of about 0.5 μm to 0.7 μm, and within the above-described range, impurities may be effectively removed, and the extract may be effectively obtained.

Thereafter, the filtered extract may be freeze-dried and prepared in a powder form, but is not limited thereto and may have various formulations.

The pharmaceutical composition according to the embodiment may be used as a medication for improving memory, improving learning ability, and improving cognitive function, and depending on a desired method, may be administered to a patient by any means, either orally or parenterally (e.g., applied intravenously, subcutaneously, intraperitoneally, or locally), and although there is no particular limitation in a dosage form, the dosage form may be determined according to the age or gender of a patient, or the severity of a disease.

Here, solid formulations for oral administration may be formulations such as acids, granules, tablets, capsules, soft capsules, pills, and the like. In addition, liquid formulations for oral use may be formulations such as suspensions, internal liquids, emulsions, syrups, gels, aerosols, and the like. Formulations for parenteral administration may be, depending on respective methods known in the art, external preparations such as acids, granules, tablets, capsules, sterilized aqueous solutions, liquids, non-aqueous solvents, suspensions, emulsions, syrups, suppositories, aerosols, and the like, or may be formulated and used in the form of sterile injectable formulations. A preferred dosage of the composition varies depending on the absorption, deactivation rate, and excretion rate of an active ingredient in the body, the age, gender and condition of a patient, and the severity of a disease to be treated, but may be appropriately selected by a person skilled in the art.

The pharmaceutical composition according to the embodiment may further include an excipient, a disintegrant, a sweetener, a lubricant, a flavoring agent, and the like, which are commonly used. For example, as the excipient, a material such as lactose, dextrose, sucrose, solbitol, mannitol, xylitol, erythritol, maltitol, starch, acacia gum, alginate, gelatin, calcium phosphate, calcium silicate, cellulose, methyl cellulose, microcrystalline cellulose, or polyvinyl pyrrolidone may be used. As the disintegrant, for example, sodium starch glycolate, crospovidone, alginic acid, carboxymethyl cellulose calcium, carboxymethyl cellulose sodium, chitosan, guar gum, low-substituted hydroxypropyl cellulose, magnesium aluminum silicate, or the like may be used.

The pharmaceutical composition may further include a pharmaceutically acceptable additive. In this case, the pharmaceutically acceptable additive may include, for example, starch, gelatinized starch, microcrystalline cellulose, lactose, povidone, colloidal silicon dioxide, calcium hydrogen phosphate, lactose, mannitol, Arabic gum, hydroxypropyl cellulose, sodium starch glycolate, carbauba wax, stearic acid, magnesium stearate, aluminum stearate, calcium stearate, white sugar, taffy, dextrose, sorbitol, talc, or the like, but is not limited thereto. The pharmaceutically acceptable additive may be included in an amount of about 0.1 parts by weight to about 90 parts by weight based on the total amount of the pharmaceutical composition.

The pharmaceutical composition may be prepared by further including one or more pharmaceutically acceptable carriers for administration. Here, the pharmaceutically acceptable carrier may be saline, sterilized water, Ringer's solution, buffered saline, dextrose solution, maltodextrin solution, glycerol, ethanol, or a mixture of one or more of these ingredients.

A medication for improving memory and improving learning ability according to one embodiment of the present invention may include the above-described pharmaceutical composition.

A health functional food composition for improving memory and improving learning ability according to one embodiment of the present invention may include, as an active ingredient, an extract of a mixed herbal medicine including Polygalae Radix, Acori Graminei Rhizoma, Platycodonis Radix, and Polygonati Rhizoma. In addition, the health functional food composition may include, as an active ingredient, an extract of a mixed herbal medicine including Polygalae Radix, Acori Graminei Rhizoma, Platycodonis Radix, Polygonati Rhizoma, and Loranthi Ramulus Et Folium.

Hereinafter, the present invention will be described in more detail with reference to Examples and Experimental Examples, but the present invention is not limited thereto.

A herbal medicine used in the following Examples, Comparative Examples, and Experimental Examples was a standard medicine purchased from Nami Pharmaceutical (Yeongcheon-si, Gyeongsangbuk-do) and used.

Example 1

A mixed herbal medicine including 20 g of Polygalae Radix, 20 g of Acori Graminei Rhizoma, 20 g of Platycodonis Radix, and 20 g of Polygonati Rhizoma was prepared, washed, and then dried.

Distilled water was added to the mixed herbal medicine to prepare 2.4 L of a composition, and then the composition was subjected to hot water extraction.

The resultant hot water extract solution was filtered using filter paper (Whatman no. 3, Maidstone, UK) and then freeze-dried to obtain an extract.

The extract was stored in a freezer maintained at about −20° C. before being used in experiments, and sterilized using a sterile filter (pore size 0.22 mm) immediately before being used in the experiments.

Example 2

Preparation for an extract was performed in the same manner as in Example 1, except that a mixed herbal medicine including 20 g of Polygalae Radix, 20 g of Acori Graminei Rhizoma, 20 g of Platycodonis Radix, 20 g of Polygonati Rhizoma, and 10 g of Loranthi Ramulus Et Folium was prepared.

Example 3

Preparation for an extract was performed in the same manner as in Example 1, except that a mixed herbal medicine including 20 g of Polygalae Radix, 20 g of Acori Graminei Rhizoma, 20 g of Platycodonis Radix, 20 g of Polygonati Rhizoma, and 20 g of Loranthi Ramulus Et Folium was prepared.

Comparative Example 1

Preparation for an extract was performed in the same manner as in Example 1, except that a mixed herbal medicine including 20 g of Polygalae Radix and 20 g of Acori Graminei Rhizoma was prepared.

Comparative Example 2

Preparation for an extract was performed in the same manner as in Example 1, except that a mixed herbal medicine including 20 g of Polygalae Radix, 20 g of Acori Graminei Rhizoma, and 20 g of Hoelen cum Pini Radix was prepared.

Comparative Example 3

Preparation for an extract was performed in the same manner as in Example 1, except that a mixed herbal medicine including 20 g of Polygalae Radix, 20 g of Acori Graminei Rhizoma, and 20 g of Platycodonis Radix was prepared.

For experiments on the compositions according to Examples 1 to 3 and Comparative Examples 1 to 3, an animal model of memory decline was created, groups were separated, the compositions were orally administered, and the efficacy of the compositions was analyzed behaviorally and histologically to confirm the effects of improving memory, learning ability, and cognitive intelligence. The behavioral analysis was performed through a Novel objective recognition (NOR) test and a Morris water maze (MWM) test, and the histological analysis was performed by confirming the expression of ChAT in a CA3 region of a hippocampus of a brain, and confirming the expression of c-fos in a paraventricular nucleus of the brain. The administration of the compositions was performed in an oral administration manner at a dose of 0.2 ml each day for a total of 21 days.

The schedules of the experiments are shown in FIG. 1. No increase and decrease in body weight due to repeated administration of herbal medicines have been confirmed.

Experimental animals used in the following experiments were 6-week-old ICR male mice (20 g to 25 g) supplied from DBL Co., Ltd. (Eumseong-gun, Chungcheongbuk-do, Korea), acclimatized for one week, and then used to create animal models. During the experimental period, the mice were allowed to freely consume a predetermined amount of solid feed and purified water, and the day/night cycle was a 12-hour cycle (Day light 08:00 to 20:00), while constant breeding conditions were maintained until the end of the experiments by maintaining an indoor temperature of about 23±2° C. and a humidity of about 50±10%.

Creation of Animal Model of Memory Decline

The ICR mice were subjected to restraint stress to induce memory decline. Specifically, the ICR mice were detained in a stress bag for 2 hours a day, each day for a total of 21 days.

Group Separation

All 56 ICR mice were divided into a normal group (Nor, n=7), a control group (Con, n=7) in which memory decline-induced ICR mice were treated with physiological saline, a group (Example 1, n=7) in which memory decline-induced ICR mice was administered with the composition according to Example 1, a group (Example 2, n=7) in which memory decline-induced ICR mice was administered with the composition according to Example 2, a group (Example 3, n=7) in which memory decline-induced ICR mice was administered with the composition according to Example 3, a group (Comparative Example 1, n=7) in which memory decline-induced ICR mice was administered with the composition according to Comparative Example 1, a group (Comparative Example 2, n=7) in which memory decline-induced ICR mice was administered with the composition according to Comparative Example 2, and a group (Comparative Example 3, n=7) in which memory decline-induced ICR mice was administered with the composition according to Comparative Example 3.

From Day 1 to Day 21 of the experiments, the composition was orally administered at 0.2 mL/animal 1 time each day for a total of 21 times, and in the case of the control group, physiological saline was administered in the same amount.

All experimental results were obtained by performing a minimum of three repeated experiments to derive an average value, and statistical significance was verified using two-way ANOVA (Bonferroni post hoc multiple comparison test) and one-way ANOVA (Tukey's test) using a GraphPad Prism 8.0 analysis program (GraphPad Software, CA, USA).

Experimental Example 1—Novel Object Recognition Test

Figure 2:
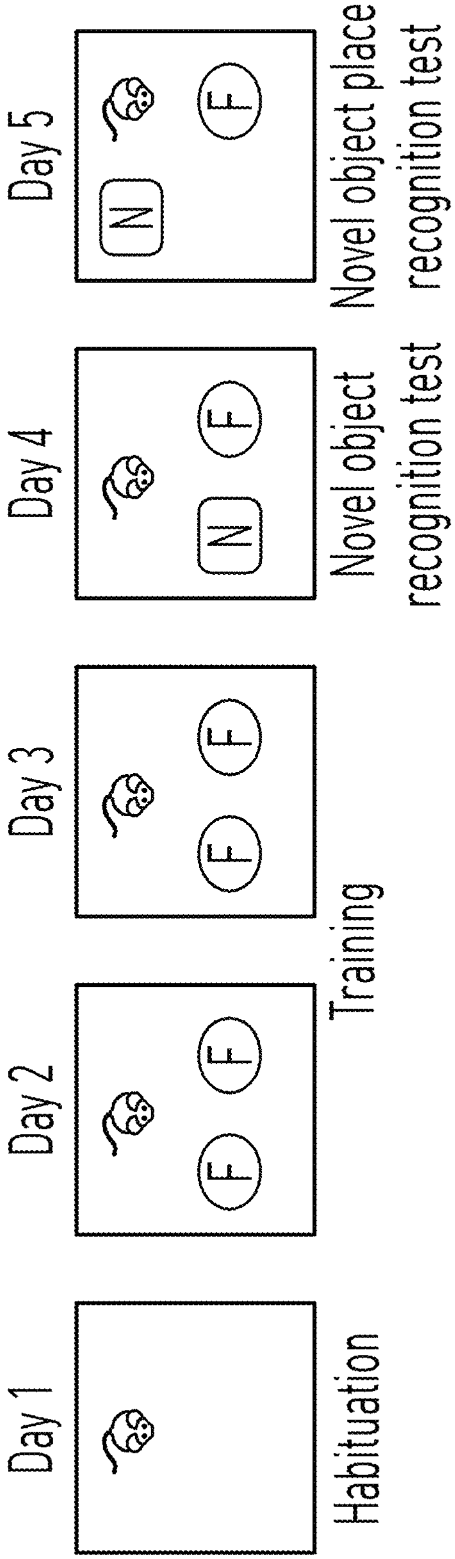
FIG. 2 is a diagram showing an experimental sequence and procedure of a Novel object recognition test.
Figure 3A:
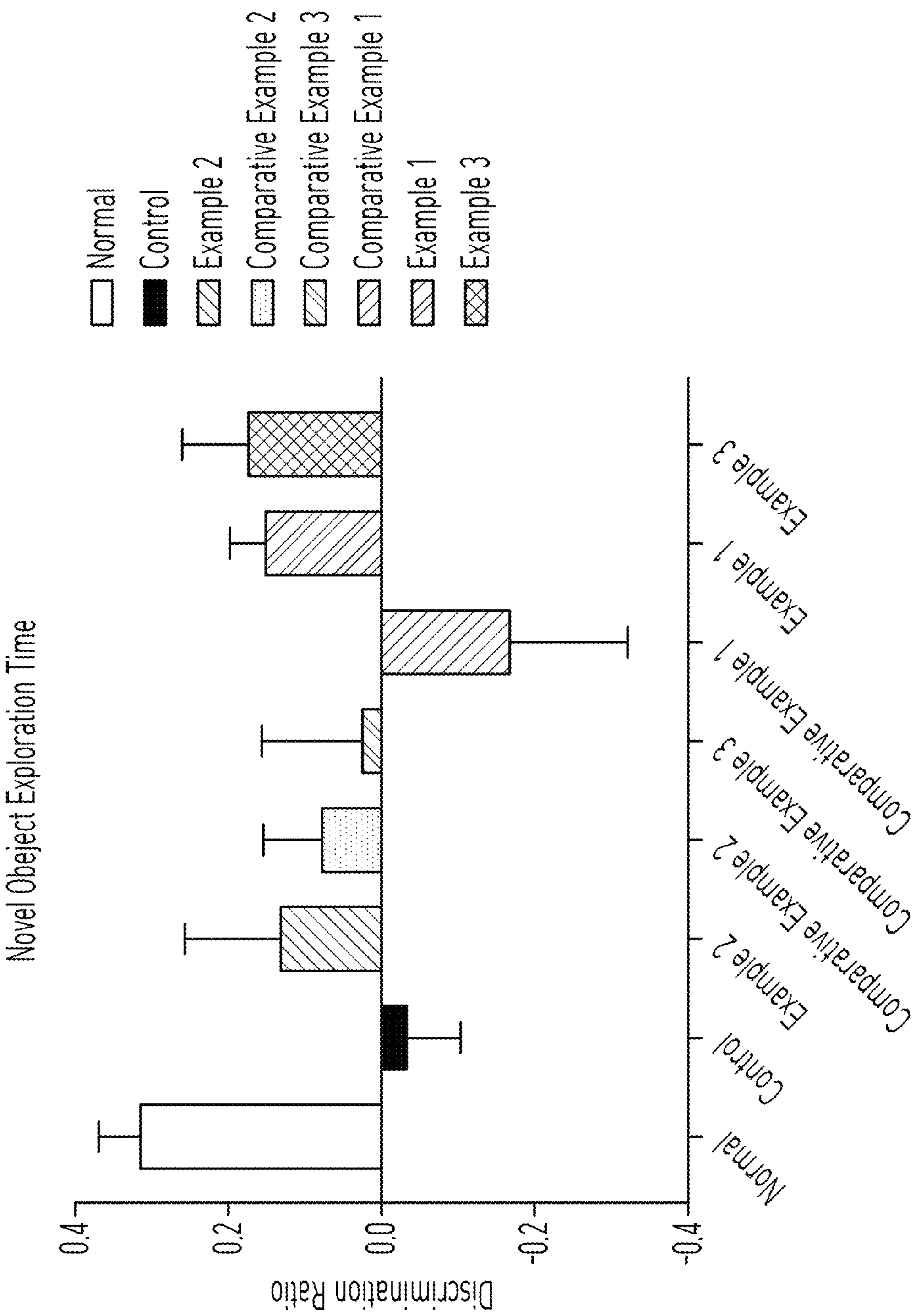
FIG. 3A is a graph showing a discrimination ratio derived by measuring the time it takes the experimental target mice to explore a novel object compared to the time it takes the experimental target mice to explore all objects in a 4-th day experiment (Novel Object Exploration Time) of Novel Object Recognition Test.

The novel objective recognition test was conducted for 5 days, from Day 10 to Day 14 of imparting restraint stress (see FIG. 2). On the first day, a mouse was placed in an open field box and acclimatized for 10 minutes. On the second and third days, two objects of the same shape and color were placed therein to acclimate the mouse to a familiar object, and the mouse was acclimated for 10 minutes. On the fourth day, one of the familiar objects was replaced with a novel object, and the response of the mouse exploring the objects was measured for 5 minutes. The time spent to explore the novel object with respect to the time spent to explore all of the objects was measured to compare values thereof. The measured values (discrimination ratio) were calculated by the following equation, and the results are shown in FIG. 3A.

$$DiscriminationRatio = \frac{t_{novel} - t_{familiar}}{t_{novel} + t_{familiar}}$$

On the 5-th day, after changing the position of the novel object, the response of the mouse exploring the object was measured for 5 minutes. The time spent to explore the novel object with respect to the time spent to explore all of the objects was measured to compare values thereof. An equation for obtaining a discrimination ratio is as follows, and the results are shown in FIG. 3B.

$$DiscriminationRatio = \frac{t_{novel} - t_{familiar}}{t_{novel} + t_{familiar}}$$

Referring to FIG. 3A, compared to the normal group, 14 days of restraint stress reduced the response to the novel object not only in the control group, but also in the groups in which the compositions according to all Examples and Comparative Examples were administered. However, in the case of the groups in which the compositions of Example 1 to Example 3 were administered, it can be confirmed that the response to the novel object was improved compared to the groups in which the compositions of Comparative Examples 1 to 3 were administered (see FIG. 3A). Particularly, in the group in which the composition of Example 3 was administered, the response to the novel object improved the most.

Figure 3B:
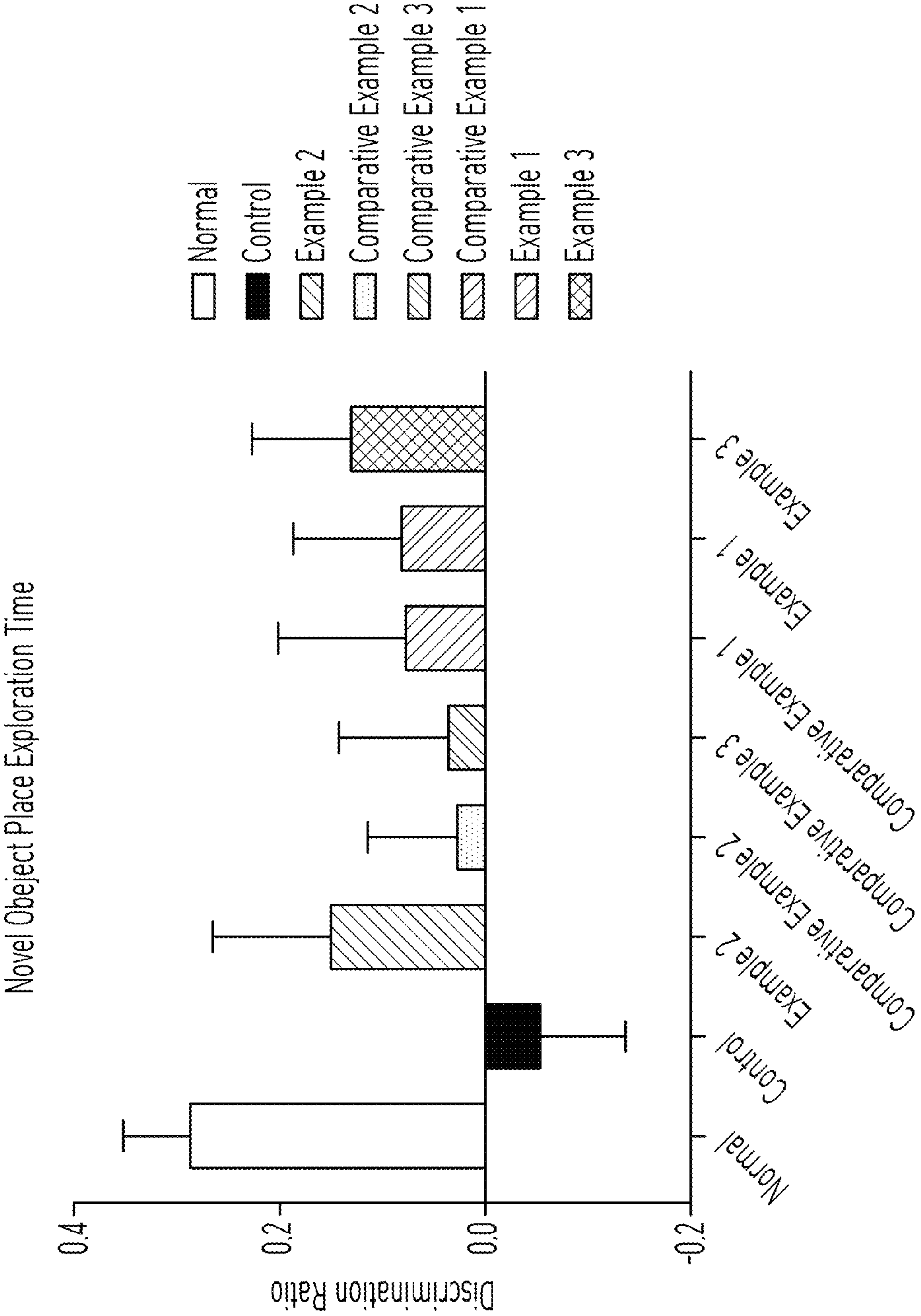
FIG. 3B is a graph showing a discrimination ratio derived by measuring the time it takes the experimental target mice to explore a novel object compared to the time it takes the experimental target mice to explore all objects in a 5-th day experiment (Novel Object Place Exploration Time) of a Novel object recognition test.

Referring to FIG. 3B, when the position of the novel object was changed, the response to the novel object at the changed position was significantly reduced in the control group in which the restraint stress was imparted and physiological saline was introduced. On the other hand, in the case of the groups in which the compositions of Example 1 and Example 3 were administered, it can be confirmed that the groups exhibited significantly better response than the other groups.

Experimental Example 2—Morris Water Maze Test

Figure 4:
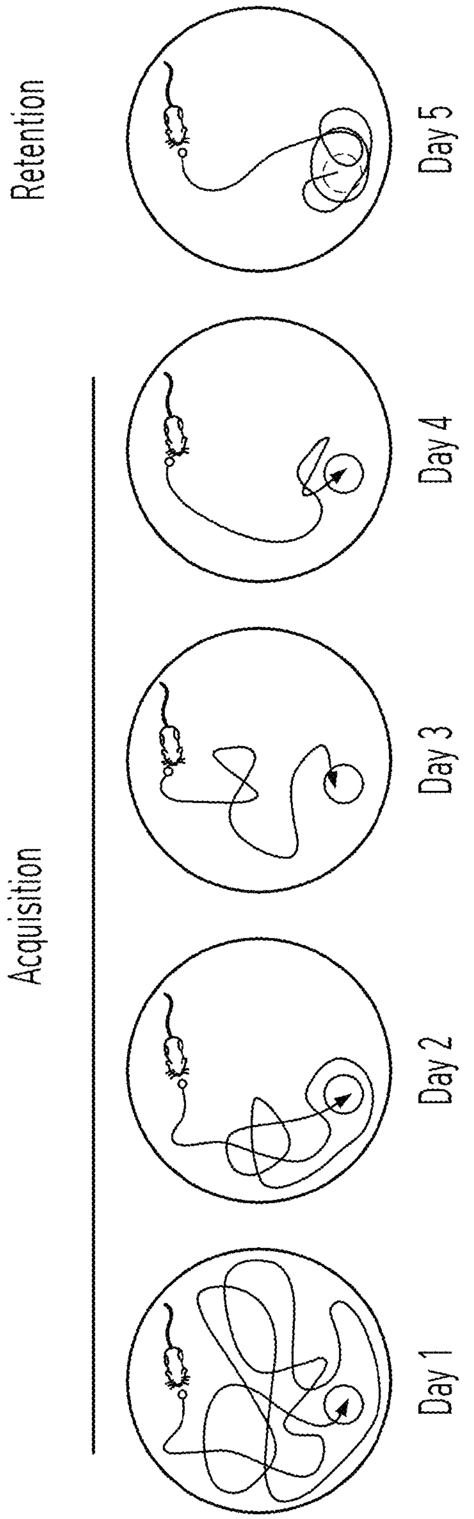
FIG. 4 is a diagram showing an experimental sequence and procedure of a Morris water maze test.

The Morris water maze test was conducted for 5 days, from Day 17 to Day 21 of imparting restraint stress (see FIG. 4).

On the first day to the fourth day, an acquisition test was performed to measure the time spent searching for a hidden platform hidden below the surface of water. After the first trial on the first day, the mouse was placed on the hidden platform, and was allowed to learn cues around a water maze for 60 seconds. If the mouse did not find the hidden platform within 60 seconds, the mouse was pulled out of the water maze. The mice pulled out of the water maze were cleaned using paper towel, and then transferred to warm home cages.

On the fifth and final day, the hidden platform was removed to perform a retention test for 60 seconds to measure latency in the place in which the hidden platform was present and the number of times the place in which the hidden platform was present was crossed.

Figure 5A:
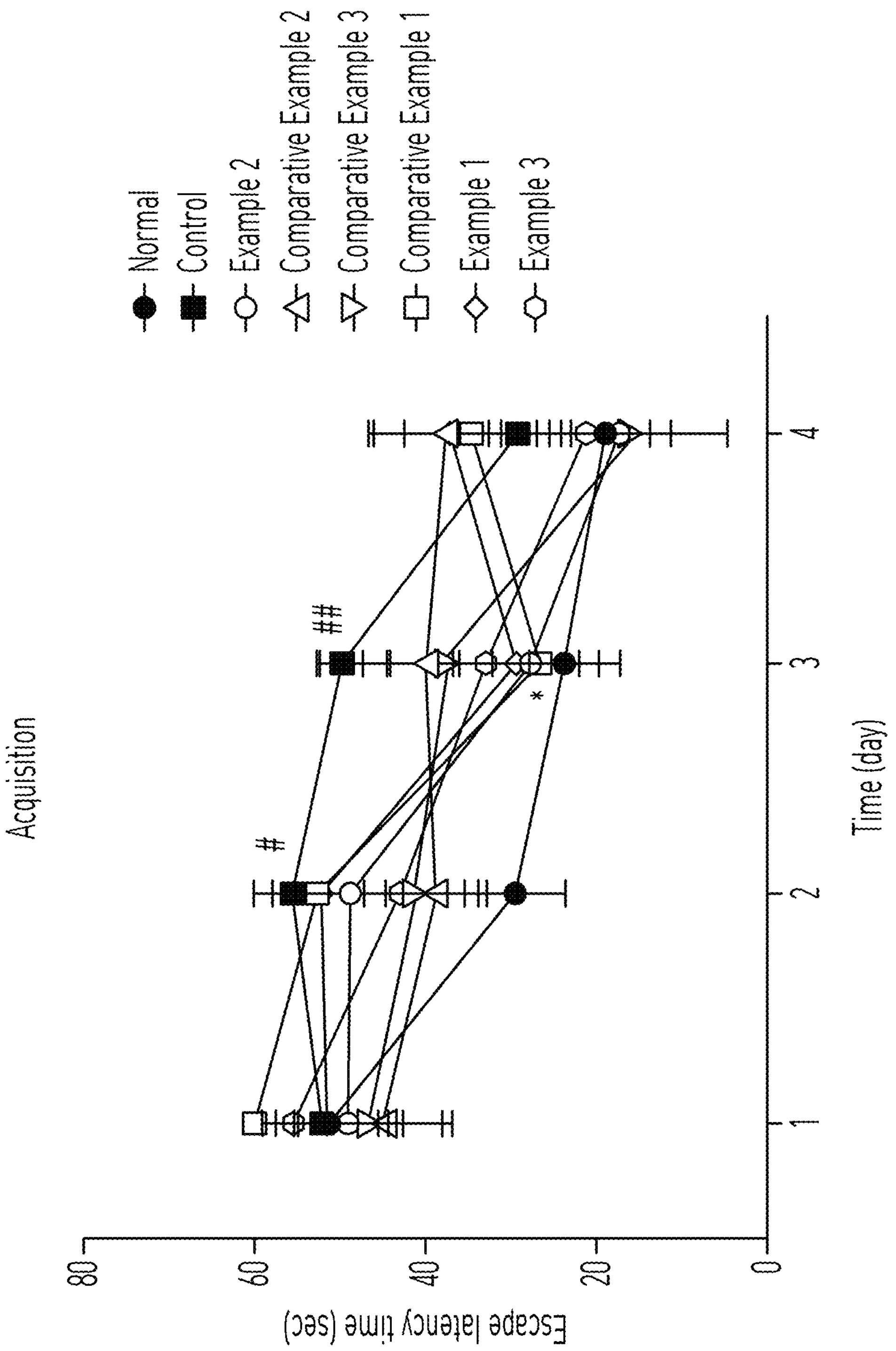
FIG. 5A is a graph showing the results of an acquisition experiment analyzed by measuring the time for finding a hidden platform in a Morris water maze test.
Figure 5B:
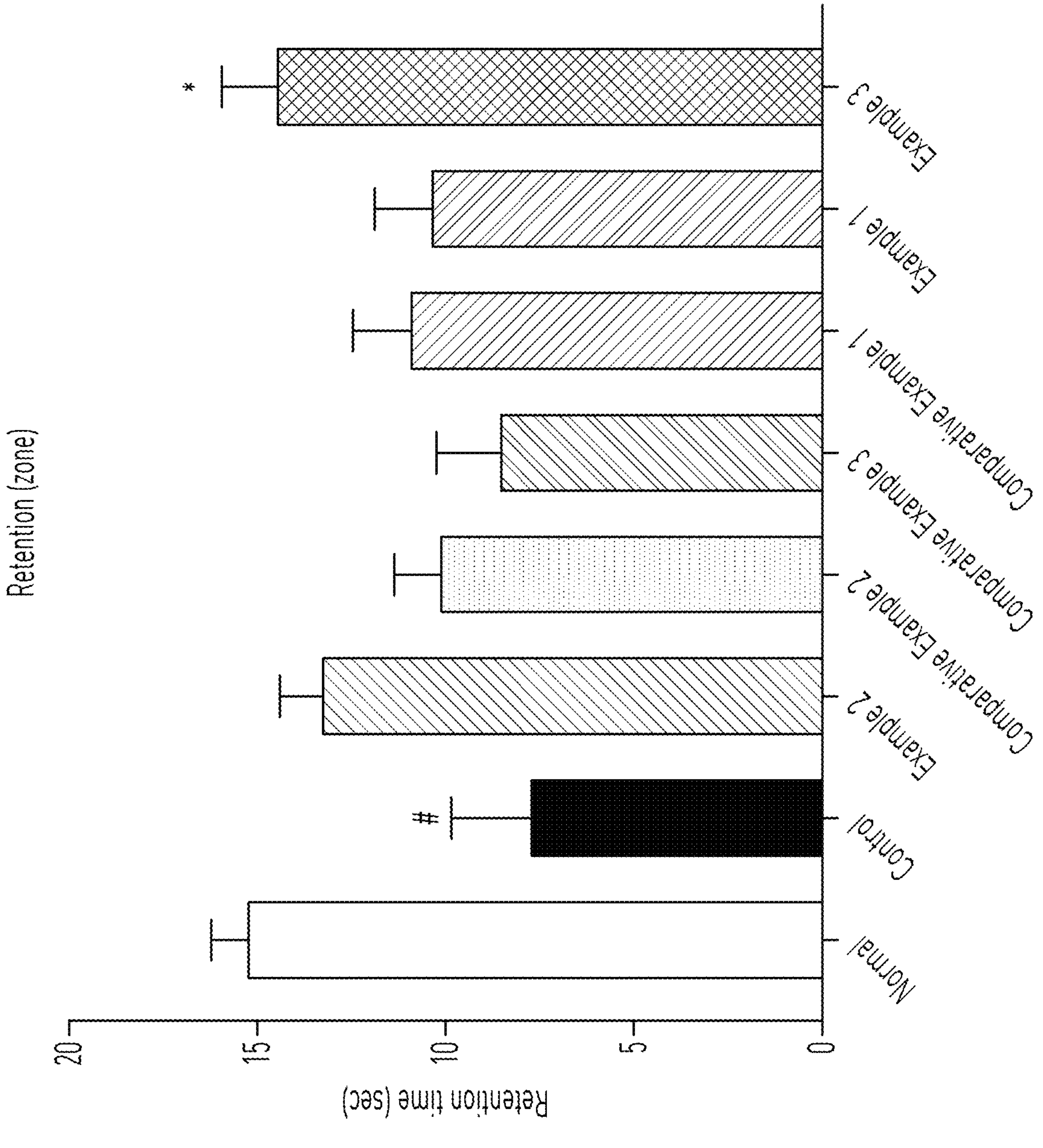
FIG. 5B is a graph showing, in a Morris water maze test, the results of comparing latency in the place in which the hidden platform was present after the hidden platform was removed.
Figure 5C:
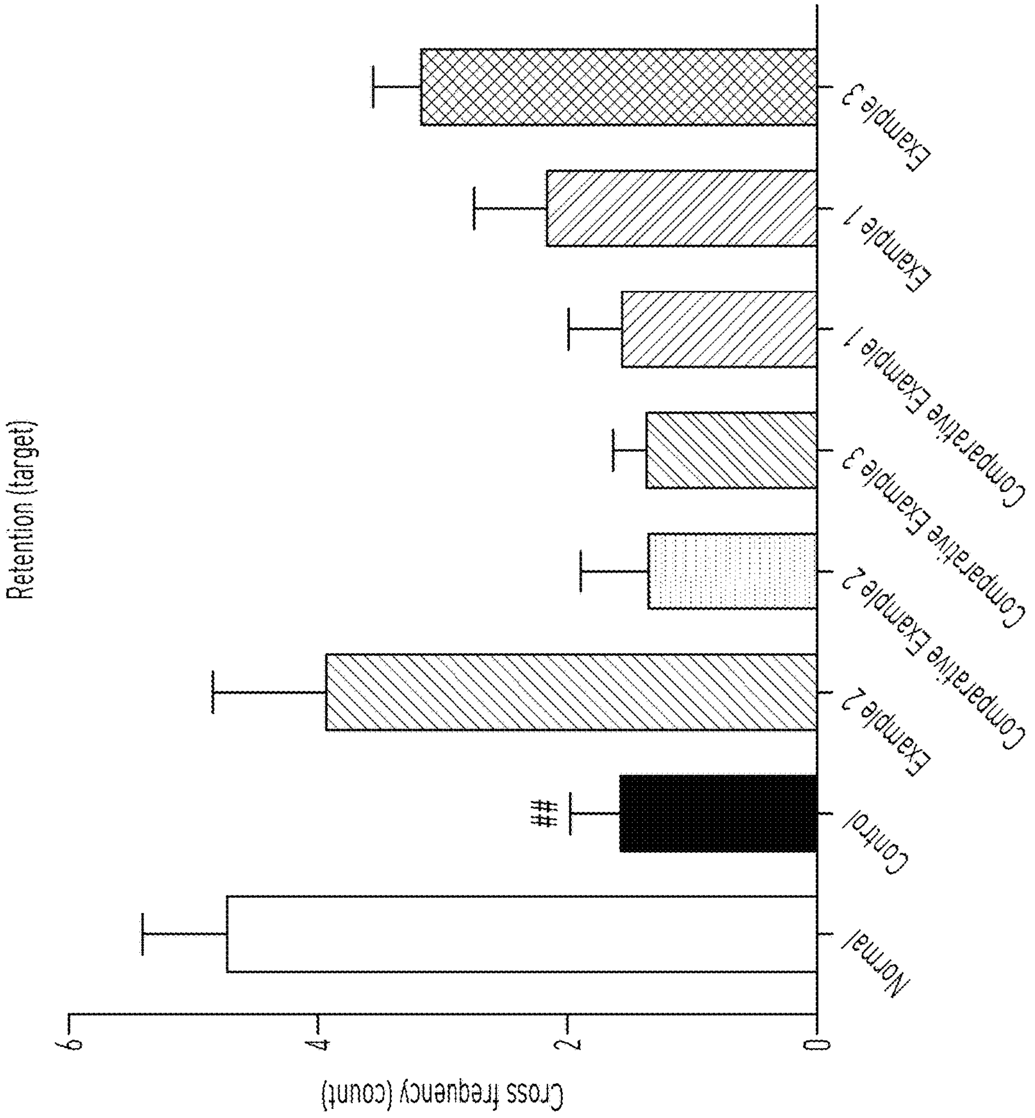
FIG. 5C is a graph showing, in a Morris water maze test, the results of comparing the number of times the place in which the hidden platform was present was crossed after the hidden platform was removed.

The results of the experiment were shown in FIG. 5A to FIG. 5C.

Referring to FIG. 5A relating to the acquisition test, the restraint stress significantly reduced the learning ability for finding the hidden platform ($p<0.05$, Day 2; $p<0.01$, Day 3). In the case of the groups in which the compositions of Example 2 and Example 3 were administered, it can be confirmed that the time spent to find the hidden platform significantly reduced from the first day to the fourth day, and particularly, in the case of the composition of Example 2, the effect of improving learning ability was better than that of the normal group.

Referring to FIG. 5B and FIG. 5C relating to the retention test, as can be confirmed in the control group, the restraint stress significantly reduced the latency in the place in which the hidden platform was present (FIG. 5B) and the number of times the place in which the hidden platform was present was crossed (FIG. 5C).

In the case of the groups in which the compositions of Example 2 and Example 3 were administered, the latency in the place in which the hidden platform was present significantly increased ($p<0.05$).

In addition, in the case of the groups in which the compositions of Example 1 to Example 3 were administered, it can be confirmed that the number of times the place in which the hidden platform was present was crossed increased, and particularly, in the case of the group in which the compositions of Example 2 and Example 3 were administered, it can be confirmed that the number of times significantly increased ($p<0.01$).

From the above-described results, it can be confirmed that the pharmaceutical composition according to the embodiments has excellent effects of improving memory and improving learning ability.

Experimental Example 3—ChAT Expression Experiment

Figure 6A:
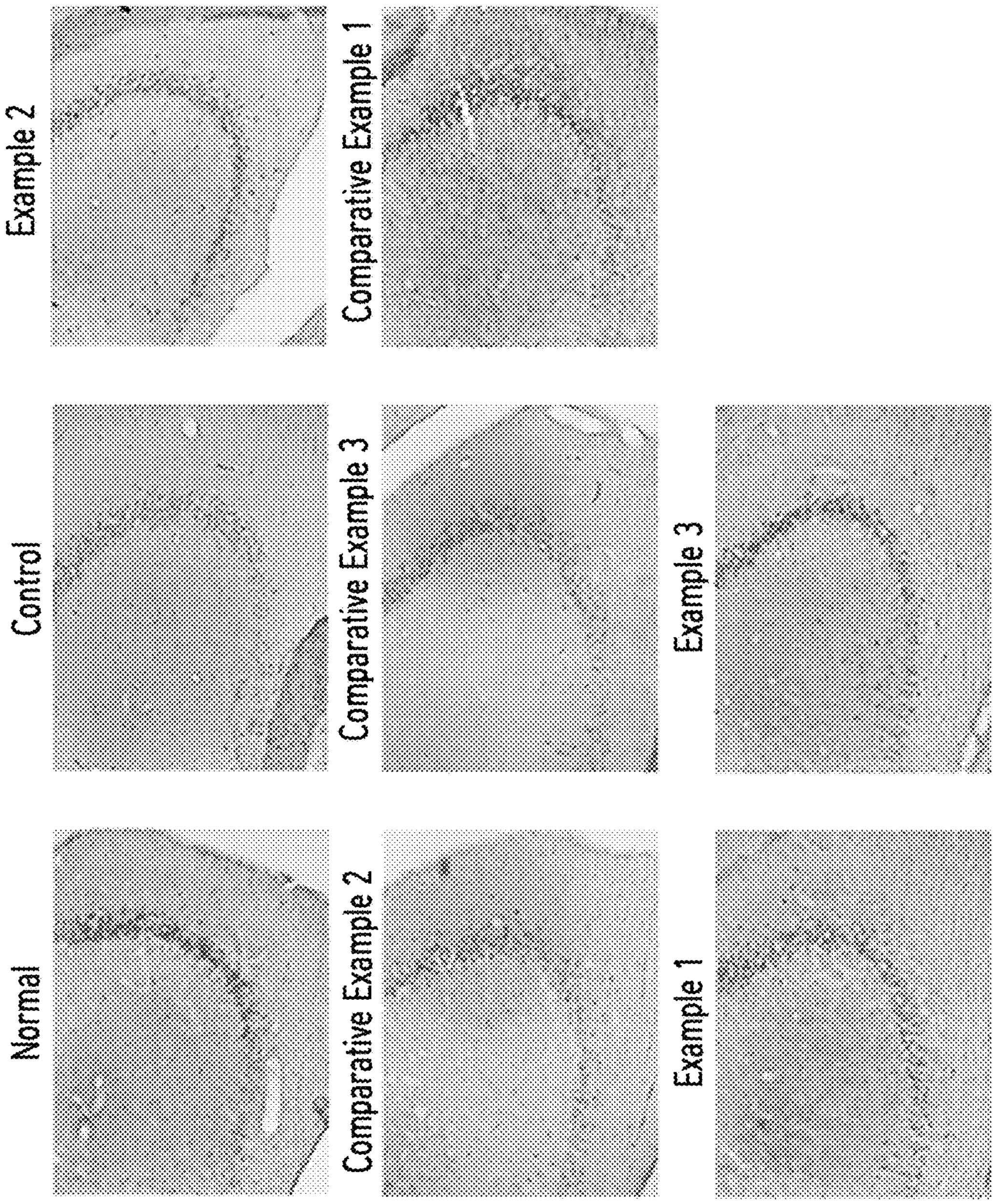
FIG. 6A shows images showing a CA3 region of a hippocampus of the brain of an experimental target mouse.
Figure 6B:
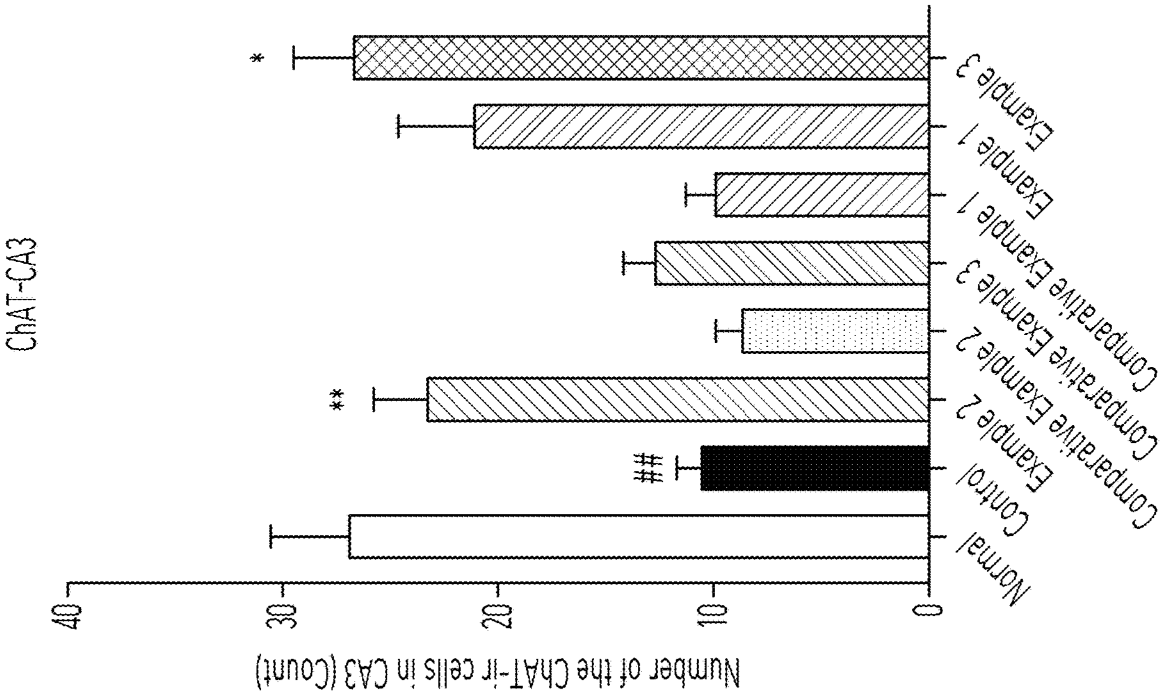
FIG. 6B is a graph showing the number of ChAT-ir cells in the CA3 region observed in FIG. 6A.

After 21 days of imparting restraint stress (after all of the experiments of Experimental Example 1 and Experimental Example 2 were completed), the expression of Choline Acetyltransferase (ChAT) was confirmed in the CA3 region of the hippocampus of the mouse's brain, and the results are shown in FIG. 6A and FIG. 6B. FIG. 6A shows images showing a CA3 region of a hippocampus of the brain of an experimental target mouse, and FIG. 6B is a graph showing the number of ChAT-ir cells in the observed CA3 region.

ChAT is an enzyme for synthesizing acetylcholine, which is a neurotransmitter in the hippocampus, and a decrease in acetylcholine in the hippocampus reduces the activity of nerve cells, resulting in reducing memory. Referring to FIG. 6A and FIG. 6B, when comparing the normal group and the control group, the restraint stress for 21 days significantly reduced the expression of ChAT in the CA3 of the hippocampus. On the other hand, in the case of the groups in which the compositions according to Examples 1 to 3 were administered, the expression of ChAT was significantly increased compared to the groups in which the compositions according to Comparative Examples 1 to 3 were administered (Example 1, $p<0.01$; Example 2, $p<0.01$; Example 3, $p<0.05$), from which it can be confirmed that the composition according to the embodiments has an effect of improving memory.

Experimental Example 4—C-fos Expression Experiment

Figure 7A:
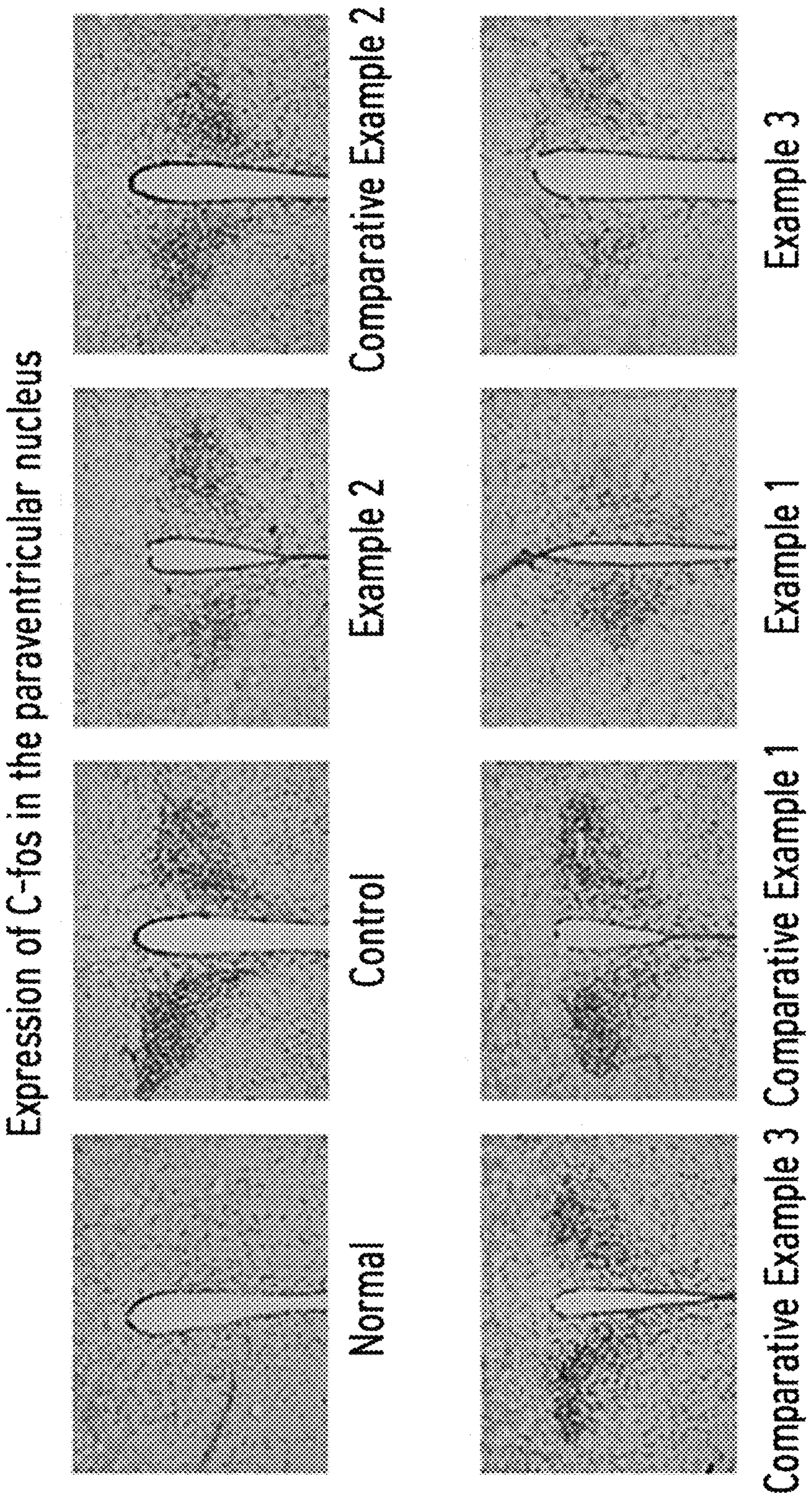
FIG. 7A shows images showing the expression of C-fos in a PVN.
Figure 7B:
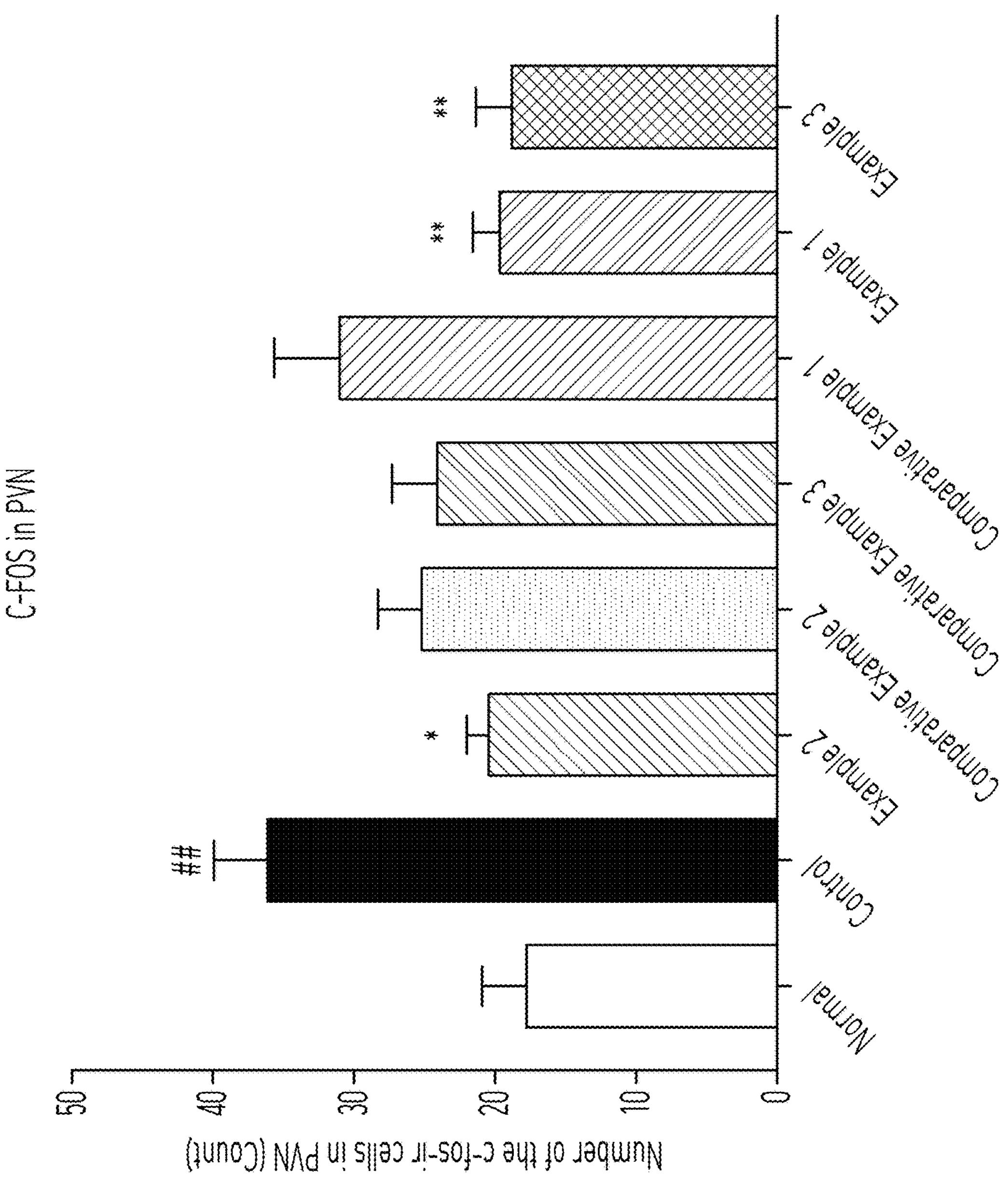
FIG. 7B is a graph showing the number of C-fos-ir cells in the PVN observed in FIG. 7A.

After 21 days of imparting restraint stress (after all of the experiments of Experimental Example 1 and Experimental Example 2 were completed), the expression of C-fos, which is an immediate early gene expression protein, was confirmed in a paraventricular nucleus (PVN) region of the mouse's brain, and the results are shown in FIG. 7A and FIG. 7B. FIG. 7A shows images showing the expression of C-fos in a PVN, and FIG. 7B is a graph showing the number of C-fos-ir cells in the PVN.

The expression of C-fos is used as an index indicating neural activity of a corresponding nerve cell. When a brain is stressed, a Hypothalamic-Pituitary-Adrenal Axis (HPA axis) is activated. When the brain is stressed, a PVN of a hypothalamus is activated, and a corticotropin-releasing hormone (CRH) is synthesized and secreted into a pituitary gland. A stimulated anterior pituitary gland secretes an adrenocorticotropic hormone (ACTH), and an adrenal cortex responds to the stimulation of the ACTH by producing cortisol, which is known as a stress hormone. The produced cortisol spreads throughout the body via the bloodstream, and induces a stress response of the body. As described above, the activation of the PVN in the stress response may play a very important role in regulating stress.

Referring to FIG. 7A and FIG. 7B, when comparing the normal group and the control group, the restraint stress for 21 days significantly increased the expression of C-fos in the PVN ($p<0.01$). On the other hand, in the case of the groups in which the compositions according to Examples 1 to 3 were administered, the expression of C-fos was significantly decreased compared to the groups in which the compositions according to Comparative Examples 1 to 3 were administered (Example 1, $p<0.01$; Example 2, $p<0.05$; Example 3, $p<0.01$). From the above-described results, it can be confirmed that the composition according to embodiments has an effect of relaxing stress.

A pharmaceutical composition according to one embodiment of the present invention may exhibit an excellent effect of improving memory, may exhibit an excellent effect of improving learning ability, may exhibit an excellent effect of improving cognitive function, may exhibit an effect of preventing and alleviating dementia and forgetfulness, and may minimize side effects.

Although the [CHONGMYUNGTANG COMPOSITION FOR IMPROVING MEMORY AND LEARNING ABILITY] has been described with reference to the specific embodiments, it is not limited thereto. Therefore, it will be readily understood by those skilled in the art that various modifications and changes can be made thereto without departing from the spirit and scope of the present invention defined by the appended claims.

What is claimed is:

1. A pharmaceutical composition for improving memory and learning ability, comprising:

an extract obtained by extracting a mixed herbal medicine consisting essentially of a defined weight ratio of Polygalae Radix, Acori Graminei Rhizoma, Platycodonis Radix, Polygonati Rhizoma, and Loranthi Ramulus Et Folium as an active ingredient, wherein said extract exhibits a synergistic enhancement of memory and learning ability relative to extracts of any individual component, and wherein in the mixed herbal medicine, the defined weight ratio of the Polygalae Radix, the Acori Graminei Rhizoma, the Platycodonis Radix, the Polygonati Rhizoma, and the Loranthi Ramulus Et Folium is 1:1:1:1:0.5 to 1.

2. A medication for use in improving memory and learning ability in a subject, comprising a pharmaceutical composition for improving memory and learning ability, comprising: an extract obtained by extracting a mixed herbal medicine consisting essentially of a defined weight ratio of Polygalae Radix, Acori Graminei Rhizoma, Platycodonis Radix, Polygonati Rhizoma, and Loranthi Ramulus Et Folium as an active ingredient, wherein said extract exhibits a synergistic enhancement of memory and learning ability relative to extracts of any individual component, and wherein in the mixed herbal medicine, the defined weight ratio of the Polygalae Radix, the Acori Graminei Rhizoma, the Platycodonis Radix, the Polygonati Rhizoma, and the Loranthi Ramulus Et Folium is 1:1:1:1:0.5 to 1.

3. A health functional food composition for improving memory and learning ability, comprising:

an extract obtained by extracting a mixed herbal medicine consisting essentially of a defined weight ratio of Polygalae Radix, Acori Graminei Rhizoma, Platycodonis Radix, Polygonati Rhizoma, and Loranthi Ramulus Et Folium as an active ingredient, wherein said extract exhibits a synergistic enhancement of memory and learning ability relative to extracts of any individual component, and wherein in the mixed herbal medicine, the defined weight ratio of the Polygalae Radix, the Acori Graminei Rhizoma, the Platycodonis Radix, the Polygonati Rhizoma, and the Loranthi Ramulus Et Folium is 1:1:1:1:0.5 to 1.

* * * * *